United States Patent [19]

Bundy

[11] 4,119,649
[45] Oct. 10, 1978

[54] ω-ARYL-9-DEOXY-9-METHYLENE-PGF-TYPE COMPOUNDS

[75] Inventor: Gordon L. Bundy, Portage, Mich.

[73] Assignee: The Upjohn Company, Kalamazoo, Mich.

[21] Appl. No.: 832,242

[22] Filed: Sep. 12, 1977

Related U.S. Application Data

[60] Division of Ser. No. 682,848, May 4, 1976, Pat. No. 4,060,534, which is a continuation-in-part of Ser. No. 651,622, Jan. 23, 1976, Pat. No. 4,021,467, which is a division of Ser. No. 556,768, Mar. 10, 1975, Pat. No. 3,950,363.

[51] Int. Cl.$^2$ .......................... C09F 7/00; C11C 3/00
[52] U.S. Cl. .............................. 260/408; 260/501.16; 260/501.18; 560/60; 562/470; 562/465
[58] Field of Search ............. 260/408, 410 P, 410.9 P, 260/413 P, 514 D, 501.16, 501.18; 560/60

[56] References Cited
U.S. PATENT DOCUMENTS
3,931,299  1/1976  Strike ................... 260/514 D

*Primary Examiner*—Winston A. Douglas
*Assistant Examiner*—John F. Niebling
*Attorney, Agent, or Firm*—Robert A. Armitage

[57] ABSTRACT

This invention comprises certain analogs PGE or 11-deoxy-PGE compounds in which the carbonyl at C-9 is replaced by methylene. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

226 Claims, No Drawings

ω-ARYL-9-DEOXY-9-METHYLENE-PGF-TYPE COMPOUNDS

The present application is a divisional application of Ser. No. 682,848, filed May 4, 1976, now issued as U.S. Pat. No. 4,060,534 on Nov. 29, 1977; which is a continuation-in-part of Ser. No. 651,622 filed Jan. 23, 1976, issued as U.S. Pat. No. 4,021,467 on May 3, 1977; which is a division of Ser. No. 556,768, filed Mar. 10, 1975, issued as U.S. Pat. No. 3,950,363 on Apr. 13, 1976.

The present invention relates to prostaglandin analogs, for which the essential material constituting disclosure therefor is incorporated by reference here from U.S. Pat. No. 4,060,534.

I claim:

1. A prostaglandin analog of the formula

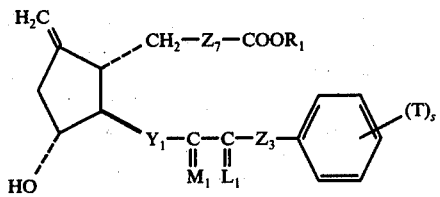

wherein $Y_1$ is trans—CH=CH—, —C≡C—, or —CH$_2$CH$_2$—, wherein $Z_3$ is oxa or methylene, $s$ is zero, one, two or 3, and T is chloro, fluoro, trifluoromethyl, alkyl of one to 3 carbon atoms, inclusive, or alkoxy of one to three carbon atoms, inclusive, with the proviso that not more than two T's are other than alkyl, the various T's being the same or different, with the further proviso that $Z_3$ is oxa only when $R_3$ and $R_4$ are hydrogen or methyl, being the same or different;

wherein $M_1$ is

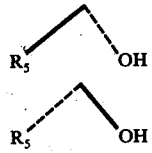

or

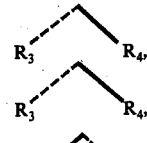

wherein $R_5$ is hydrogen or methyl;
wherein $L_1$ is

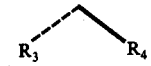

or a mixture of and wherein $R_3$ and $R_4$ are hydrogen, methyl, or fluoro, being the same or different, with the proviso that one of $R_3$ and $R_4$ is fluoro only when the other is hydrogen or fluoro, and
wherein $Z_7$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —C≡C—CH$_2$—(CH$_2$)$_g$—CH$_2$—, and
(8) —CH$_2$—C≡C—(CH$_2$)$_g$—CH$_2$—,
wherein $g$ is one, 2, or 3; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A prostaglandin analog according to claim 1, wherein $Y_1$ is —CH$_2$CH$_2$—.

3. A prostaglandin analog according to claim 2, wherein $Z_7$ is cis—CH=CH—CH$_2$—(CH$_2$)$_g$—CF$_2$—.

4. 9-Deoxy-9-methylene-2,2-difluoro-13,14-dihydro-17-phenyl-18,19,20-trinor-PGF$_2$, a prostaglandin analog according to claim 3.

5. A prostaglandin analog according to claim 2, wherein $Z_7$ is —(CH$_2$)$_3$—(CH$_2$)$_g$—CF$_2$—.

6. 9-Deoxy-9-methylene-2,2-difluoro-13,14-dihydro-17-phenyl-18,19,20-trinor-PGF$_1$, a prostaglandin analog according to claim 5.

7. A prostaglandin analog according to claim 2, wherein $Z_7$ is cis—CH$_2$—CH=CH—(CH$_2$)$_g$—CH$_2$—.

8. 9-Deoxy-9-methylene-cis-4,5-didehydro-13,14-dihydro-17-phenyl-18,19,20-trinor-PGF$_1$, a prostaglandin analog according to claim 7.

9. A prostaglandin analog according to claim 2, wherein $Z_7$ is —CH$_2$—O—CH$_2$—(CH$_2$)$_g$—CH$_2$—.

10. 9-Deoxy-9-methylene-5-oxa-13,14-dihydro-17-phenyl-18,19,20-trinor-PGF$_1$, a prostaglandin analog according to claim 9.

11. A prostaglandin analog according to claim 2, wherein $Z_7$ is —CH$_2$—C≡C—(CH$_2$)$_g$—CH$_2$—.

12. 9-Deoxy-9-methylene-5,6-didehydro-13,14-dihydro-17-phenyl-18,19,20-trinor-PGF$_2$, a prostaglandin analog according to claim 11.

13. A prostaglandin analog according to claim 2, wherein $Z_7$ is —CH$_2$—C≡C—(CH$_2$)$_g$—CH$_2$—.

14. 9-Deoxy-9-methylene-4,4,5,5-tetradehydro-13,14-dihydro-17-phenyl-18,19,20-trinor-PGF$_2$, a prostaglandin analog according to claim 13.

15. A prostaglandin analog according to claim 2, wherein $Z_7$ is —(CH$_2$)$_3$—(CH$_2$)$_g$—CH$_2$—.

16. A prostaglandin analog according to claim 15, wherein $M_1$ is

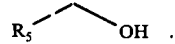

17. 9-Deoxy-9-methylene-15-epi-13,14-dihydro-17-phenyl-18,19,20-trinor-PGF$_1$, a prostaglandin analog according to claim 16.

18. A prostaglandin analog according to claim 15, wherein $M_1$ is

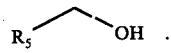

19. A prostaglandin analog according to claim 18, wherein $Z_3$ is methylene, $s$ is zero or one, and T is chloro, fluoro, or trifluoromethyl.

20. A prostaglandin analog according to claim 19, wherein g is 3.

21. 9-Deoxy-9-methylene-2a,2b-dihomo-15-methyl-13,14-dihydro-17-phenyl-18,19,20-trinor-PGF$_1$, a prostaglandin analog according to claim 20.

22. 9-Deoxy-9-methylene-2a,2b-dihomo-13,14-dihydro-17-phenyl-18,19,20-trinor-PGF$_1$, a prostaglandin analog according to claim 20.

23. A prostaglandin analog according to claim 19, wherein g is one.

24. A prostaglandin analog according to claim 23, wherein at least one of $R_3$ and $R_4$ is methyl.

25. A prostaglandin analog according to claim 24, wherein $R_3$ and $R_4$ are both methyl.

26. 9-Deoxy-9-methylene-16,16-dimethyl-13,14-dihydro-17-phenyl-18,19,20-trinor-PGF$_1$, a prostaglandin analog according to claim 25.

27. A prostaglandin analog according to claim 23, wherein at least one of $R_3$ and $R_4$ is fluoro.

28. A prostaglandin analog according to claim 27, wherein $R_3$ and $R_4$ are both fluoro.

29. 9-Deoxy-9-methylene-16,16-difluoro-13,14-dihydro-17-phenyl-18,19,20-trinor-PGF$_1$, a prostaglandin analog according to claim 28.

30. A prostaglandin analog according to claim 23, wherein $R_3$ and $R_4$ are both hydrogen.

31. A prostaglandin analog according to claim 30, wherein $R_5$ is methyl.

32. 9-Deoxy-9-methylene-15-methyl-13,14-dihydro-17-phenyl-18,19,20-trinor-PGF$_1$, a prostaglandin analog according to claim 31.

33. A prostaglandin analog according to claim 30, wherein $R_5$ is hydrogen.

34. 9-Deoxy-9-methylene-13,14-dihydro-17-phenyl-18,19,20-trinor-PGF$_1$, a prostaglandin analog according to claim 33.

35. A prostaglandin analog according to claim 2, wherein $Z_7$ is cis—CH=CH—CH$_2$—(CH$_2$)$_g$—CH$_2$—.

36. A prostaglandin analog according to claim 35, wherein $M_1$ is

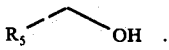

37. A prostaglandin analog according to claim 36, wherein $Z_3$ is methylene, s is zero or one, and T is chloro, fluoro, or trifluoromethyl.

38. A prostaglandin analog according to claim 37, wherein g is 3.

39. 9-Deoxy-9-methylene-2a,2b-dihomo-15-epi-15-methyl-13,14-dihydro-17-phenyl-18,19,20-trinor-PGF$_2$, a prostaglandin analog according to claim 38.

40. 9-Deoxy-9-methylene-2a,2b-dihomo-15-epi-13,14-dihydro-17-phenyl-18,19,20-trinor-PGF$_2$, a prostaglandin analog according to claim 38.

41. A prostaglandin analog according to claim 37, wherein g is one.

42. A prostaglandin analog according to claim 41, wherein at least one of $R_3$ and $R_4$ is methyl.

43. 9-Deoxy-9-methylene-15-epi-16,16-dimethyl-13,14-dihydro-17-phenyl-18,19,20-trinor-PGF$_2$, a prostaglandin analog according to claim 42.

44. A prostaglandin analog according to claim 41, wherein at least one of $R_3$ and $R_4$ is fluoro.

45. 9-Deoxy-9-methylene-15-epi-16,16-difluoro-13,14-dihydro-17-phenyl-18,19,20-trinor-PGF$_2$, a prostaglandin analog according to claim 44.

46. A prostaglandin analog according to claim 41, wherein $R_3$ and $R_4$ are both hydrogen.

47. 9-Deoxy-9-methylene-15-epi-15-methyl-13,14-dihydro-17-phenyl-18,19,20-trinor-PGF$_2$, a prostaglandin analog according to claim 46.

48. A prostaglandin analog according to claim 35, wherein $M_1$ is

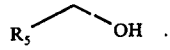

49. A prostaglandin analog according to claim 48, wherein $Z_3$ is methylene, s is zero or one, and T is chloro, fluoro, or trifluoromethyl.

50. A prostaglandin analog according to claim 49, wherein g is 3.

51. A prostaglandin analog according to claim 50, wherein at least one of $R_3$ and $R_4$ is methyl.

52. 9-Deoxy-9-methylene-2a,2b-dihomo-16,16-dimethyl-13,14-dihydro-17-phenyl-18,19,20-trinor-PGF$_2$, a prostaglandin analog according to claim 51.

53. A prostaglandin analog according to claim 50, wherein at least one of $R_3$ and $R_4$ is fluoro.

54. 9-Deoxy-9-methylene-2a,2b-dihomo-16,16-difluoro-13,14-dihydro-17-phenyl-18,19,20-trinor-PGF$_2$, a prostaglandin analog according to claim 53.

55. A prostaglandin analog according to claim 50, wherein $R_3$ and $R_4$ are both hydrogen.

56. 9-Deoxy-9-methylene-2a,2b-dihomo-15-methyl-13,14-dihydro-17-phenyl-18,19,20-trinor-PGF$_2$, a prostaglandin analog according to claim 55.

57. A prostaglandin analog according to claim 49, wherein g is one.

58. A prostaglandin analog according to claim 57, wherein at least one of $R_3$ and $R_4$ is methyl.

59. A prostaglandin analog according to claim 58, wherein $R_3$ and $R_4$ are both methyl.

60. 9-Deoxy-9-methylene-16,16-dimethyl-13,14-dihydro-17-phenyl-18,19,20-trinor-PGF$_2$, tris-(hydroxymethyl)aminomethane salt, a prostaglandin analog according to claim 59.

61. 9-Deoxy-9-methylene-16,16-dimethyl-13,14-dihydro-17-phenyl-18,19,20-trinor-PGF$_2$, methyl ester, a prostaglandin analog according to claim 59.

62. 9-Deoxy-9-methylene-16,16-dimethyl-13,14-dihydro-17-phenyl-18,19,20-trinor-PGF$_2$, a prostaglandin analog according to claim 59.

63. A prostaglandin analog according to claim 57, wherein at least one of $R_3$ and $R_4$ is fluoro.

64. A prostaglandin analog according to claim 63, wherein $R_3$ and $R_4$ are both fluoro.

65. A prostaglandin analog according to claim 64, wherein $R_5$ is methyl.

66. 9-Deoxy-9-methylene-15-methyl-16,16-difluoro-13,14-dihydro-17-phenyl-18,19,20-trinor-PGF$_2$, a prostaglandin analog according to claim 65.

67. A prostaglandin analog according to claim 64, wherein $R_5$ is hydrogen.

68. 9-Deoxy-9-methylene-16,16-difluoro-13,14-dihydro-17-phenyl-18,19,20-trinor-PGF$_2$, a prostaglandin analog according to claim 67.

69. A prostaglandin analog according to claim 57, wherein $R_3$ and $R_4$ are both hydrogen.

70. A prostaglandin analog according to claim 69, wherein $R_5$ is methyl.

71. 9-Deoxy-9-methylene-15-methyl-13,14-dihydro-17-phenyl-18,19,20-trinor-PGF$_2$, tris-(hydroxymethyl- )aminomethane salt, a prostaglandin analog according to claim 70.

72. 9-Deoxy-9-methylene-15-methyl-13,14-dihydro-17-phenyl-18,19,20-trinor-PGF$_2$, methyl ester, a prostaglandin analog according to claim 70.

73. 9-Deoxy-9-methylene-15-methyl-13,14-dihydro-17-phenyl-18,19,20-trinor-PGF$_2$, a prostaglandin analog according to claim 70.

74. A prostaglandin analog according to claim 69, wherein R$_5$ is hydrogen.

75. 9-Deoxy-9-methylene-13,14-dihydro-17-phenyl-18,19,20-trinor-PGF$_2$, a methyl ester, a prostaglandin analog according to claim 74.

76. 9-Deoxy-9-methylene-13,14-dihydro-17-phenyl-18,19,20-trinor-PGF$_2$, a prostaglandin analog according to claim 74.

77. A prostaglandin analog according to claim 1, wherein Y$_1$ is —C≡C—.

78. A prostaglandin analog according to claim 77, wherein Z$_7$ is cis—CH=CH—CH$_2$—(CH$_2$)$_g$—CF$_2$—.

79. 9-Deoxy-9-methylene-2,2-difluoro-13,14-didehydro-17-phenyl-18,19,20-trinor-PGF$_2$, a prostaglandin analog according to claim 78.

80. A prostaglandin analog according to claim 77, wherein Z$_7$ is —(CH$_2$)$_3$—(CH$_2$)$_g$—CF$_2$—.

81. 9-Deoxy-9-methylene-2,2-difluoro-13,14-didehydro-17-phenyl-18,19,20-trinor-PGF$_1$, a prostaglandin analog according to claim 80.

82. A prostaglandin analog according to claim 77, wherein Z$_7$ is cis—CH$_2$—CH=CH—(CH$_2$)$_g$—CH$_2$—.

83. 9-Deoxy-9-methylene-cis-4,5-didehydro-13,14-didehydro-17-phenyl-18,19,20-trinor-PGF$_1$, a prostaglandin analog according to claim 82.

84. A prostaglandin analog according to claim 77, wherein Z$_7$ is —CH$_2$—O—CH$_2$—(CH$_2$)$_g$—CH$_2$—.

85. 9-Deoxy-9-methylene-5-oxa-13,14-didehydro-17-phenyl-18,19,20-trinor-PGF$_1$, a prostaglandin analog according to claim 84.

86. A prostaglandin analog according to claim 77, wherein Z$_7$ is —C≡C—CH$_2$—(CH$_2$)$_g$—CH$_2$—.

87. 9-Deoxy-9-methylene-5,6,13,14-tetradehydro-17-phenyl-18,19,20-trinor-PGF$_2$, a prostaglandin analog according to claim 86.

88. A prostaglandin analog according to claim 77, wherein Z$_7$ is —CH$_2$—C≡C—(CH$_2$)$_g$—CH$_2$—.

89. 9-Deoxy-9-methylene-4,4,5,5,13,14-hexadehydro-17-phenyl-18,19,20-trinor-PGF$_1$, a prostaglandin analog according to claim 88.

90. A prostaglandin analog according to claim 77, wherein Z$_7$ is —(CH$_2$)$_3$—(CH$_2$)$_g$—CH$_2$—.

91. A prostaglandin analog according to claim 90, wherein M$_1$ is

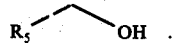

92. 9-Deoxy-9-methylene-15-epi-13,14-didehydro-17-phenyl-18,19,20-trinor-PGF$_1$, a prostaglandin analog according to claim 91.

93. A prostaglandin analog according to claim 90, wherein M$_1$ is

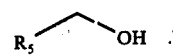

94. A prostaglandin analog according to claim 93, wherein Z$_3$ is methylene, s is zero or one, and T is chloro, fluoro, or trifluoromethyl.

95. A prostaglandin analog according to claim 94, wherein g is 3.

96. 9-Deoxy-9-methylene-2a,2b-dihomo-15-methyl-13,14-didehydro-17-phenyl-18,19,20-trinor-PGF$_1$, a prostaglandin analog according to claim 95.

97. 9-Deoxy-9-methylene-2a,2b-dihomo-13,14-didehydro-17-phenyl-18,19,20-trinor-PGF$_1$, a prostaglandin analog according to claim 95.

98. A prostaglandin analog according to claim 94, wherein g is one.

99. A prostaglandin analog according to claim 98, wherein at least one of R$_3$ and R$_4$ is methyl.

100. A prostaglandin analog according to claim 99, wherein R$_3$ and R$_4$ are both methyl.

101. 9-Deoxy-9-methylene-16,16-dimethyl-13,14-didehydro-17-phenyl-18,19,20-trinor-PGF$_1$, a prostaglandin analog according to claim 100.

102. A prostaglandin analog according to claim 98, wherein at least one of R$_3$ and R$_4$ is fluoro.

103. A prostaglandin analog according to claim 102, wherein R$_3$ and R$_4$ are both fluoro.

104. 9-Deoxy-9-methylene-16,16-difluoro-13,14-didehydro-17-phenyl-18,19,20-trinor-PGF$_1$, a prostaglandin analog according to claim 103.

105. A prostaglandin analog according to claim 98, wherein R$_3$ and R$_4$ are both hydrogen.

106. A prostaglandin analog according to claim 105, wherein R$_5$ is methyl.

107. 9-Deoxy-9-methylene-15-methyl-13,14-didehydro-17-phenyl-18,19,20-trinor-PGF$_1$, a prostaglandin analog according to claim 106.

108. A prostaglandin analog according to claim 105, wherein R$_5$ is hydrogen.

109. 9-Deoxy-9-methylene-13,14-didehydro-17-phenyl-18,19,20-trinor-PGF$_1$, a prostaglandin analog according to claim 108.

110. A prostaglandin analog according to claim 77, wherein Z$_7$ is cis—CH=CH—CH$_2$—(CH$_2$)$_g$—CH$_2$—.

111. A prostaglandin analog according to claim 110, wherein M$_1$ is

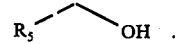

112. A prostaglandin analog according to claim 111, wherein Z$_3$ is methylene, s is zero or one, and T is chloro, fluoro, or trifluoromethyl.

113. A prostaglandin analog according to claim 112, wherein g is 3.

114. 9-Deoxy-9-methylene-2a,2b-dihomo-15-epi-15-methyl-13,14-didehydro-17-phenyl-18,19,20-trinor-PGF$_2$, a prostaglandin analog according to claim 113.

115. 9-Deoxy-9-methylene-2a,2b-dihomo-15-epi-13,14-didehydro-17-phenyl-18,19,20-trinor-PGF$_2$, a prostaglandin analog according to claim 113.

116. A prostaglandin analog according to claim 112, wherein g is one.

117. A prostaglandin analog according to claim 116, wherein at least one of R$_3$ and R$_4$ is methyl.

118. 9-Deoxy-9-methylene-15-epi-16,16-dimethyl-13,14-didehydro-17-phenyl-18,19,20-trinor-PGF$_2$, a prostaglandin analog according to claim 117.

119. A prostaglandin analog according to claim 116, wherein at least one of R$_3$ and R$_4$ is fluoro.

120. 9-Deoxy-9-methylene-15-epi-16,16-difluoro-13,14-didehydro-17-phenyl-18,19,20-trinor-PGF$_2$, a prostaglandin analog according to claim 119.

121. A prostaglandin analog according to claim 116, wherein R$_3$ and R$_4$ are both hydrogen.

122. 9-Deoxy-9-methylene-15-epi-15-methyl-13,14-didehydro-17-phenyl-18,19,20-trinor-PGF$_2$, a prostaglandin analog according to claim 121.

123. A prostaglandin analog according to claim 110, wherein M$_1$ is

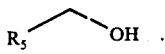

124. A prostaglandin analog according to claim 123, wherein Z$_3$ is methylene, $s$ is zero or one, and T is chloro, fluoro, or trifluoromethyl.

125. A prostaglandin analog according to claim 124, wherein $g$ is 3.

126. A prostaglandin according to claim 125, wherein at least one of R$_3$ and R$_4$ is methyl.

127. 9-Deoxy-9-methylene-2a,2b-dihomo-16,16-dimethyl-13,14-didehydro-17-phenyl-18,19,20-trinor-PGF$_2$, a prostaglandin analog according to claim 126.

128. A prostaglandin analog according to claim 125, wherein at least one of R$_3$ and R$_4$ is fluoro.

129. 9-Deoxy-9-methylene-2a,2b-dihomo-16,16-difluoro-13,14-didehydro-17-phenyl-18,19,20-trinor-PGF$_2$, a prostaglandin analog according to claim 128.

130. A prostaglandin analog according to claim 125, wherein R$_3$ and R$_4$ are both hydrogen.

131. 9-Deoxy-9-methylene-2a,2b-dihomo-15-methyl-13,14-didehydro-17-phenyl-18,19,20-trinor-PGF$_2$, a prostaglandin analog according to claim 130.

132. A prostaglandin analog according to claim 124, wherein $g$ is one.

133. A prostaglandin analog according to claim 132, wherein at least one of R$_3$ and R$_4$ is methyl.

134. A prostaglandin analog according to claim 133, wherein R$_3$ and R$_4$ are both methyl.

135. 9-Deoxy-9-methylene-16,16-dimethyl-13,14-didehydro-17-phenyl-18,19,20-trinor-PGF$_2$, tris-(hydroxymethyl)aminomethane salt, a prostaglandin analog according to claim 134.

136. 9-Deoxy-9-methylene-16,16-dimethyl-13,14-didehydro-17-phenyl-18,19,20-trinor-PGF$_2$, methyl ester, a prostaglandin analog according to claim 134.

137. 9-Deoxy-9-methylene-16,16-dimethyl-13,14-didehydro-17-phenyl-18,19,20-trinor-PGF$_2$, a prostaglandin analog according to claim 134.

138. A prostaglandin analog according to claim 132, wherein at least one of R$_3$ and R$_4$ is fluoro.

139. A prostaglandin analog according to claim 138, wherein R$_3$ and R$_4$ are both fluoro.

140. A prostaglandin analog according to claim 139, wherein R$_5$ is methyl.

141. 9-Deoxy-9-methylene-15-methyl-16,16-difluoro-13,14-didehydro-17-phenyl-18,19,20-trinor-PGF$_2$, a prostaglandin analog according to claim 140.

142. A prostaglandin analog according to claim 139, wherein R$_5$ is hydrogen.

143. 9-Deoxy-9-methylene-16,16-difluoro-13,14-didehydro-17-phenyl-18,19,20-trinor-PGF$_2$, a prostaglandin analog according to claim 142.

144. A prostaglandin analog according to claim 132, wherein R$_3$ and R$_4$ are both hydrogen.

145. A prostaglandin analog according to claim 144, wherein R$_5$ is methyl.

146. 9-Deoxy-9-methylene-15-methyl-13,14-didehydro-17-phenyl-18,19,20-trinor-PGF$_2$, tris-(hydroxymethyl)aminomethane salt, a prostaglandin analog according to claim 145.

147. 9-Deoxy-9-methylene-15-methyl-13,14-didehydro-17-phenyl-18,19,20-trinor-PGF$_2$, methyl ester, a prostaglandin analog according to claim 145.

148. 9-Deoxy-9-methylene-15-methyl-13,14-didehydro-17-phenyl-18,19,20-trinor-PGF$_2$, a prostaglandin analog according to claim 145.

149. A prostaglandin analog according to claim 144, wherein R$_5$ is hydrogen.

150. 9-Deoxy-9-methylene-13,14-didehydro-17-phenyl-18,19,20-trinor-PGF$_2$, methyl ester, a prostaglandin analog according to claim 149.

151. 9-Deoxy-9-methylene-13,14-didehydro-17-phenyl-18,19,20-trinor-PGF$_2$, a prostaglandin analog according to claim 149.

152. A prostaglandin analog according to claim 1, wherein Y$_1$ is trans—CH=CH—.

153. A prostaglandin analog according to claim 152, wherein Z$_7$ is cis—CH=CH—CH$_2$—(CH$_2$)$_g$—CF$_2$—.

154. 9-Deoxy-9-methylene-2,2-difluoro-17-phenyl-18,19,20-trinor-PGF$_2$, a prostaglandin analog according to claim 153.

155. A prostaglandin analog according to claim 152, wherein Z$_7$ is —(CH$_2$)$_3$—(CH$_2$)$_g$—CF$_2$—.

156. 9-Deoxy-9-methylene-2,2-difluoro-17-phenyl-18,19,20-trinor-PGF$_1$, a prostaglandin analog according to claim 155.

157. A prostaglandin analog according to claim 152, wherein Z$_7$ is cis—CH$_2$—CH=CH—(CH$_2$)$_g$—CH$_2$—.

158. 9-Deoxy-9-methylene-cis-4,5-didehydro-17-phenyl-18,19,20-trinor-PGF$_1$, a prostaglandin analog according to claim 157.

159. A prostaglandin analog according to claim 152, wherein Z$_7$ is —CH$_2$—O—CH$_2$—(CH$_2$)$_g$—CH$_2$—.

160. 9-Deoxy-9-methylene-5-oxa-17-phenyl-18,19,20-trinor-PGF$_1$, a prostaglandin analog according to claim 159.

161. A prostaglandin analog according to claim 152, wherein Z$_7$ is —C≡C—CH$_2$—(CH$_2$)$_g$—CH$_2$—.

162. 9-Deoxy-9-methylene-5,6-didehydro-17-phenyl-18,19,20-trinor-PGF$_2$, a prostaglandin analog according to claim 161.

163. A prostaglandin analog according to claim 152, wherein Z$_7$ is —CH$_2$—C≡C—(CH$_2$)$_g$—CH$_2$.

164. 9-Deoxy-9-methylene-4,4,5,5-tetradehydro-17-phenyl-18,19,20-trinor-PGF$_1$, a prostaglandin analog according to claim 163.

165. A prostaglandin analog according to claim 152, wherein Z$_7$ is —(CH$_2$)$_3$—(CH$_2$)$_g$—CH$_2$—.

166. A prostaglandin analog according to claim 165, wherein M$_1$ is

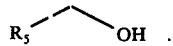

167. 9-Deoxy-9-methylene-15-epi-17-phenyl-18,19,20-trinor-PGF$_1$, a prostaglandin analog according to claim 166.

168. A prostaglandin analog according to claim 165, wherein M$_1$ is

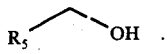

169. A prostaglandin analog according to claim 168, wherein $Z_3$ is methylene, $s$ is zero or one, and T is chloro, fluoro, or trifluoromethyl.

170. A prostaglandin analog according to claim 169, wherein $g$ is 3.

171. 9-Deoxy-9-methylene-2a,2b-dihomo-15-methyl-17-phenyl-18,19,20-trinor-PGF$_1$, a prostaglandin analog according to claim 170.

172. 9-Deoxy-9-methylene-2a,2b-dihomo-17-phenyl-18,19,20-trinor-PGF$_1$, a prostaglandin analog according to claim 170.

173. A prostaglandin analog according to claim 169, wherein $g$ is one.

174. A prostaglandin analog according to claim 173, wherein at least one of $R_3$ and $R_4$ is methyl.

175. A prostaglandin analog according to claim 174, wherein $R_3$ and $R_4$ are both methyl.

176. 9-Deoxy-9-methylene-16,16-dimethyl-17-phenyl-18,19,20-trinor-PGF$_1$, a prostaglandin analog according to claim 175.

177. A prostaglandin analog according to claim 173, wherein at least one of $R_3$ and $R_4$ is fluoro.

178. A prostaglandin analog according to claim 177, wherein $R_3$ and $R_4$ are both fluoro.

179. 9-Deoxy-9-methylene-16,16-difluoro-17-phenyl-18,19,20-trinor-PGF$_1$, a prostaglandin analog according to claim 178.

180. A prostaglandin analog according to claim 173, wherein $R_3$ and $R_4$ are both hydrogen.

181. A prostaglandin analog according to claim 180, wherein $R_5$ is methyl.

182. 9-Deoxy-9-methylene-15-methyl-17-phenyl-18,19,20-trinor-PGF$_1$, a prostaglandin analog according to claim 181.

183. A prostaglandin analog according to claim 180, wherein $R_5$ is hydrogen.

184. 9-Deoxy-9-methylene-17-phenyl-18,19,20-trinor-PGF$_1$, a prostaglandin analog according to claim 183.

185. A prostaglandin analog according to claim 152, wherein $Z_7$ is cis—CH=CH—CH$_2$—(CH$_2$)$_g$—CH$_2$—.

186. A prostaglandin analog according to claim 185, wherein $M_1$ is

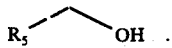

187. A prostaglandin analog according to claim 186, wherein $Z_3$ is methylene, $s$ is zero or one, and T is chloro, fluoro, or trifluoromethyl.

188. A prostaglandin analog according to claim 187, wherein $g$ is 3.

189. 9-Deoxy-9-methylene-2a,2b-dihomo-15-epi-15-methyl-17-phenyl-18,19,20-trinor-PGF$_2$, a prostaglandin analog according to claim 188.

190. 9-Deoxy-9-methylene-2a,2b-dihomo-15-epi-17-phenyl-18,19,20-trinor-PGF$_2$, a prostaglandin analog according to claim 188.

191. A prostaglandin analog according to claim 187, wherein $g$ is one.

192. A prostaglandin analog according to claim 191, wherein at least one of $R_3$ and $R_4$ is methyl.

193. 9-Deoxy-9-methylene-15-epi-16,16-dimethyl-17-phenyl-18,19,20-trinor-PGF$_2$, a prostaglandin analog according to claim 192.

194. A prostaglandin analog according to claim 191, wherein at least one of $R_3$ and $R_4$ is fluoro.

195. 9-Deoxy-9-methylene-15-epi-16,16-difluoro-17-phenyl-18,19,20-trinor-PGF$_2$, a prostaglandin analog according to claim 194.

196. A prostaglandin analog according to claim 191 wherein $R_3$ and $R_4$ are both hydrogen.

197. 9-Deoxy-9-methylene-15-methyl-17-phenyl-18,19,20-trinor-PGF$_2$, a prostaglandin analog according to claim 196.

198. A prostaglandin analog according to claim 185, wherein $M_1$ is

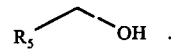

199. A prostaglandin analog according to claim 198, wherein $Z_3$ is methylene, $s$ is zero or one, and T is chloro, fluoro, or trifluoromethyl.

200. A prostaglandin analog according to claim 199, wherein $g$ is 3.

201. A prostaglandin analog according to claim 200, wherein at least one of $R_3$ and $R_4$ is methyl.

202. 9-Deoxy-9-methylene-2a,2b-dihomo-16,16-dimethyl-17-phenyl-18,19,20-trinor-PGF$_2$, a prostaglandin analog according to claim 201.

203. A prostaglandin analog according to claim 200, wherein at least one of $R_3$ and $R_4$ is fluoro.

204. 9-Deoxy-9-methylene-2a,2b-dihomo-16,16-difluoro-17-phenyl-18,19,20-trinor-PGF$_2$, a prostaglandin analog according to claim 203.

205. A prostaglandin analog according to claim 200, wherein $R_3$ and $R_4$ are both hydrogen.

206. 9-Deoxy-9-methylene-2a,2b-dihomo-15-methyl-17-phenyl-18,19,20-trinor-PGF$_2$, a prostaglandin analog according to claim 205.

207. A prostaglandin analog according to claim 199, wherein $g$ is one.

208. A prostaglandin analog according to claim 207, wherein at least one of $R_3$ and $R_4$ is methyl.

209. A prostaglandin analog according to claim 208, wherein $R_3$ and $R_4$ are both methyl.

210. 9-Deoxy-9-methylene-16,16-dimethyl-17-phenyl-18,19,20-trinor-PGF$_2$, tris-(hydroxymethyl)aminomethane salt, a prostaglandin analog according to claim 209.

211. 9-Deoxy-9-methylene-16,16-dimethyl-17-phenyl-18,19,20-trinor-PGF$_2$, methyl ester, a prostaglandin analog according to claim 209.

212. 9-Deoxy-9-methylene-16,16-dimethyl-17-phenyl-18,19,20-trinor-PGF$_2$, a prostaglandin in analog according to claim 209.

213. A prostaglandin analog according to claim 207, wherein at least one of $R_3$ and $R_4$ is fluoro.

214. A prostaglandin analog according to claim 213, wherein $R_3$ and $R_4$ are both fluoro.

215. A prostaglandin analog according to claim 214, wherein $R_5$ is methyl.

216. 9-Deoxy-9-methylene-15-methyl-16,16-difluoro-17-phenyl-18,19,20-trinor-PGF$_2$, a prostaglandin analog according to claim 215.

217. A prostaglandin analog according to claim 214, wherein $R_5$ is hydrogen.

218. 9-Deoxy-9-methylene-16,16-difluoro-17-phenyl-18,19,20-trinor-PGF$_2$, a prostaglandin analog according to claim 217.

219. A prostaglandin analog according to claim 207, wherein R$_3$ and R$_4$ are both hydrogen.

220. A prostaglandin analog according to claim 219, wherein R$_5$ is methyl.

221. 9-Deoxy-9-methylene-15-methyl-17-phenyl-18,19,20-trinor-PGF$_2$, tris-(hydroxymethyl)aminomethane salt, a prostaglandin analog according to claim 220.

222. 9-Deoxy-9-methylene-15-methyl-17-phenyl-18,19,20-trinor-PGF$_2$, methyl ester, a prostaglandin analog according to claim 220.

223. 9-Deoxy-9-methylene-15-methyl-17-phenyl-18,19,20-trinor-PGF$_2$, a prostaglandin analog according to claim 220.

224. A prostaglandin analog according to claim 219, wherein R$_5$ is hydrogen.

225. 9-Deoxy-9-methylene-17-phenyl-18,19,20-trinor-PGF$_2$, methyl ester, a prostaglandin analog according to claim 224.

226. 9-Deoxy-9-methylene-17-phenyl-18,19,20-trinor-PGF$_2$, a prostaglandin analog according to claim 224.

* * * * *

UNITED STATES PATENT OFFICE
CERTIFICATE OF CORRECTION

Patent No. 4,119,649  Dated October 10, 1978

Inventor(s) Gordon L. Bundy

It is certified that error appears in the above-identified patent and that said Letters Patent are hereby corrected as shown below:

Column 1, lines 48-52, should read as follows:

-- wherein $L_1$ is

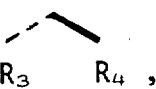

$R_3 \quad R_4$ ,

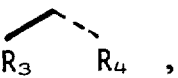

$R_3 \quad R_4$ ,

Signed and Sealed this

Twentieth Day of March 1979

[SEAL]

Attest:

RUTH C. MASON
*Attesting Officer*

DONALD W. BANNER
*Commissioner of Patents and Trademarks*